(12) United States Patent
Qandah et al.

(10) Patent No.: US 12,318,082 B2
(45) Date of Patent: Jun. 3, 2025

(54) RETRACTOR SYSTEM

(71) Applicant: Nicholas A. Qandah, New Hartford, NY (US)

(72) Inventors: Nicholas A. Qandah, New Hartford, NY (US); Melissa D. Coale, Chester, NJ (US)

(73) Assignee: Nicholas A. Qandah, New Hartford, NY (US)

( * ) Notice: Subject to any disclaimer, the term of this patent is extended or adjusted under 35 U.S.C. 154(b) by 200 days.

(21) Appl. No.: 18/146,159

(22) Filed: Dec. 23, 2022

(65) Prior Publication Data

US 2023/0380827 A1    Nov. 30, 2023

Related U.S. Application Data

(63) Continuation of application No. 15/695,079, filed on Sep. 5, 2017, now Pat. No. 11,534,153.

(51) Int. Cl.
*A61B 17/02* (2006.01)
*A61M 29/00* (2006.01)
*A61B 17/00* (2006.01)

(52) U.S. Cl.
CPC ...... *A61B 17/0293* (2013.01); *A61B 17/0206* (2013.01); *A61M 29/00* (2013.01); *A61B 2017/0046* (2013.01)

(58) Field of Classification Search
CPC .................. A61B 17/0206; A61B 17/0293
See application file for complete search history.

(56) References Cited

U.S. PATENT DOCUMENTS

| | | | | |
|---|---|---|---|---|
| 5,931,777 A | * | 8/1999 | Sava ................. | A61B 17/02 600/210 |
| 2005/0192484 A1 | * | 9/2005 | Sharratt ............ | A61B 17/0293 600/210 |
| 2013/0245383 A1 | * | 9/2013 | Friedrich .......... | A61B 17/0293 600/228 |
| 2014/0039264 A1 | * | 2/2014 | Heiman ............ | A61B 17/0218 600/210 |
| 2015/0313585 A1 | * | 11/2015 | Abidin .............. | A61B 17/025 600/219 |
| 2016/0081681 A1 | * | 3/2016 | Waugh .............. | A61B 34/20 606/279 |

FOREIGN PATENT DOCUMENTS

WO    WO-2015116624 A1 *  8/2015    ....... A61B 17/00234

\* cited by examiner

*Primary Examiner* — Nicholas J Plionis
(74) *Attorney, Agent, or Firm* — UB Greensfelder LLP; Matthew J. Schonauer

(57) ABSTRACT

Systems and methods of use are provided that allow improved instrumentation and access during a surgical procedure including for instance a lateral approach minimally invasive spinal fusion procedure.

19 Claims, 8 Drawing Sheets

Figure 3
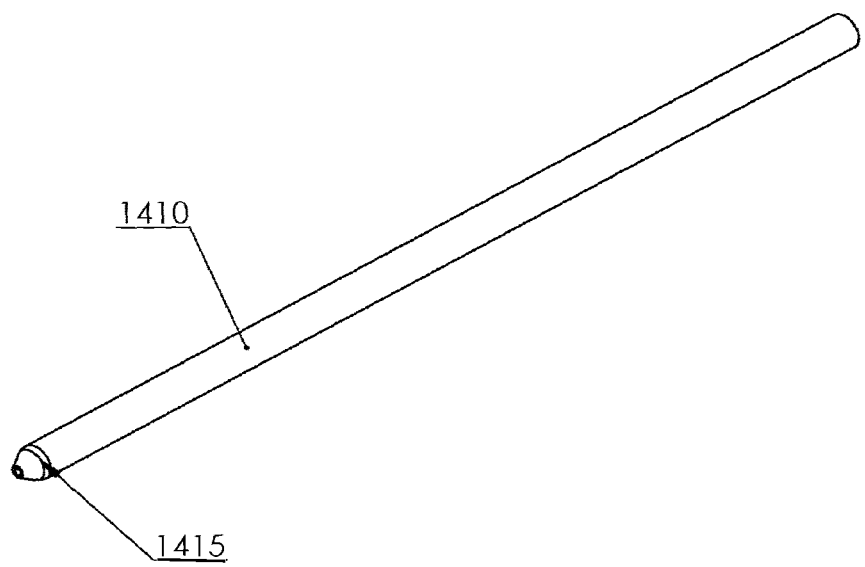
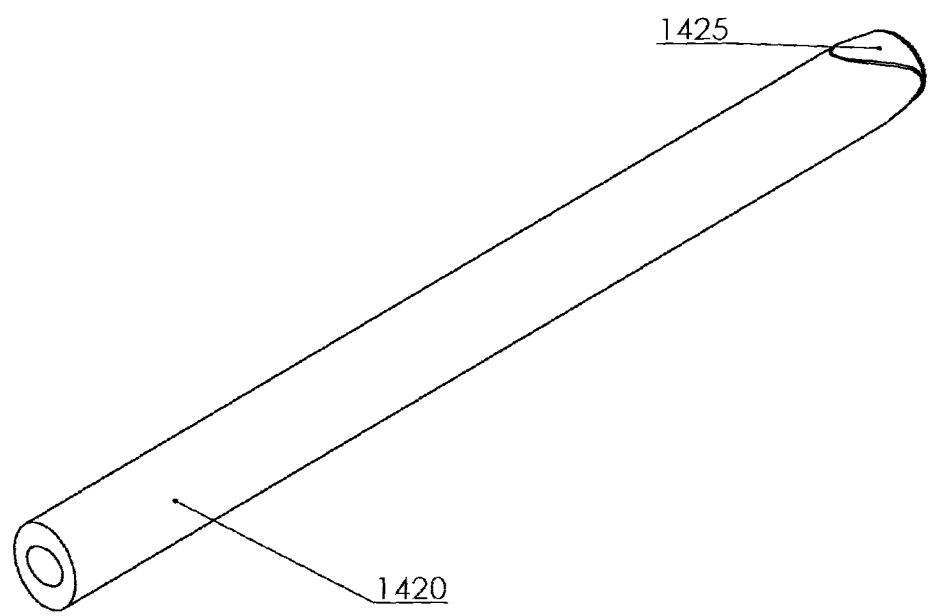
Figure 4

RETRACTOR SYSTEM

CROSS-REFERENCE TO RELATED APPLICATIONS

This application claims the benefit under 35 USC § 120 of U.S. Nonprovisional application Ser. No. 15/695,079 filed 5 Sep. 2017, the content of which is hereby incorporated by reference as if fully recited herein.

TECHNICAL FIELD

Exemplary embodiments of the present invention relate generally to mechanical devices and their use, and more specifically to devices used in connection with surgical procedures.

BACKGROUND OF THE INVENTION

In the field of surgery in general and lateral approach spine surgery in particular, it is often beneficial to have retractor instruments which are capable of a multi-stepped approach, with each respective step serving a distinct function in the procedure. To that end, devices applicable for at least a lateral approach minimally invasive lumbar spine fusion are provided. Although the devices of the present invention are described in relation to spine surgery specifically, they are relevant and usable within many other surgical fields where access below large portions of tissue or musculature are helpful to a surgeon.

BRIEF SUMMARY OF THE INVENTION

According to certain embodiments of the present disclosure, a retractor system includes; a handheld retractor having a blade disposed upon a first end portion thereof, a handle disposed upon a second portion thereof, and a first engagement feature disposed therebetween; ring retractor having a substantially rigid generally planar armature enclosing at least part of an area defining an operative site, a plurality of articulated blades coupled to the armature, and a second engagement feature disposed upon a distal face of the armature; wherein the first engagement feature and second engagement feature are complementary structures sized and shaped for rigidly coupling the ring retractor upon the handheld retractor after the handheld retractor has been positioned by an operator.

According to further embodiments of the present disclosure, the first engagement feature is a post and the second engagement feature is a complementary aperture.

According to further embodiments of the present disclosure, the first engagement feature is the outside profile of a portion of the handheld retractor and the second engagement feature is a complementary recess in the ring retractor wherein the shape of the recess substantially approximates the outside profile of the handheld retractor.

According to further embodiments of the present disclosure, the first engagement feature is a post having an internal thread.

According to certain embodiments of the present disclosure; a handheld retractor includes a blade disposed upon a first end portion thereof, a handle disposed upon a second portion thereof, and a first engagement feature disposed therebetween; ring retractor having a substantially rigid armature enclosing at least part of an area defining an operative site, a plurality of articulated blades coupled to the armature, and a second engagement feature disposed upon a distal face of the armature; wherein the first engagement feature and second engagement feature are complementary structures sized and shaped for rigidly coupling the ring retractor upon the handheld retractor after the handheld retractor has been positioned by an operator wherein the first and second engagement features are configured for the armature to be mountable in a proximal orientation upon the handheld retractor.

According to further embodiments of the present disclosure, the handheld retractor is a Deaver Retractor.

BRIEF DESCRIPTION OF THE SEVERAL VIEWS OF THE DRAWINGS

In the figures, which are not necessarily drawn to scale, like numerals describe substantially similar components throughout the several views. The drawings illustrate generally, by way of example, but not by way of limitation, various embodiments discussed in the claims of the present document.

FIG. 3 shows a perspective view of a dilator.
FIG. 4 shows a perspective view of a dilator.

DETAILED DESCRIPTION OF THE INVENTION

Figure 2B:
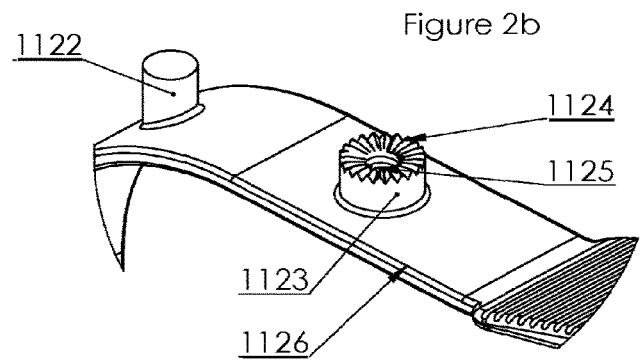
FIG. 2b shows an enlarged perspective view of several coupling features disposed upon a handheld retractor.

Various embodiments of the presently disclosed apparatus will now be described in detail with reference to the drawings, wherein like reference numerals identify similar or identical elements. In the drawings and in the description that follows, the term "proximal," will refer to the end of a device or system that is closest to the operator, while the term "distal" will refer to the end of the device or system that is farthest from the operator. Similar, anatomical terms of reference such as dorsal, lateral, anterior, and sagittal shall have their accepted meanings in the arts.

Figure 10A:
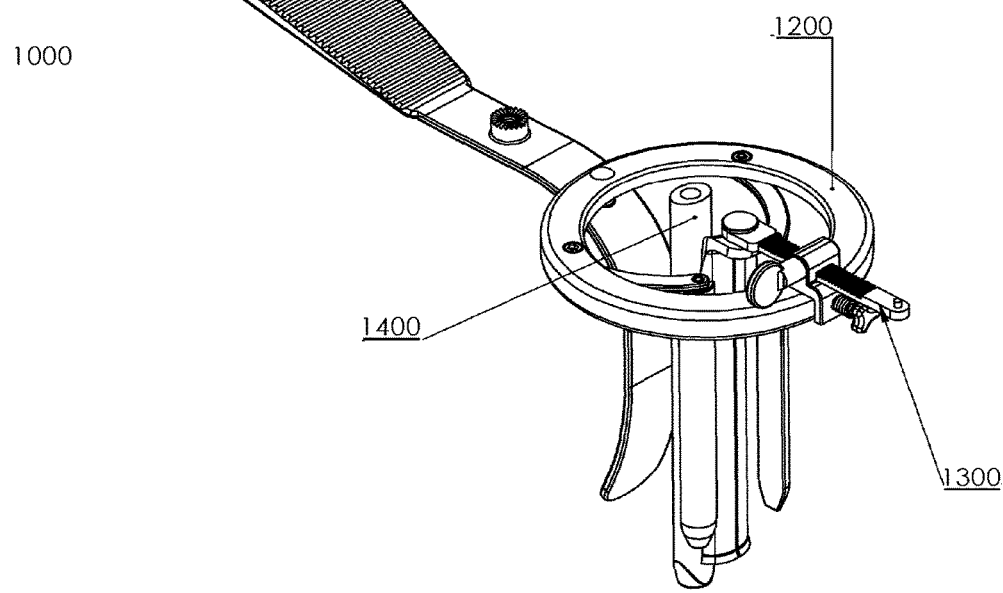
FIG. 10a shows a perspective view of a third step in the assembly of an embodiment of a Retractor System.
Figure 10B:
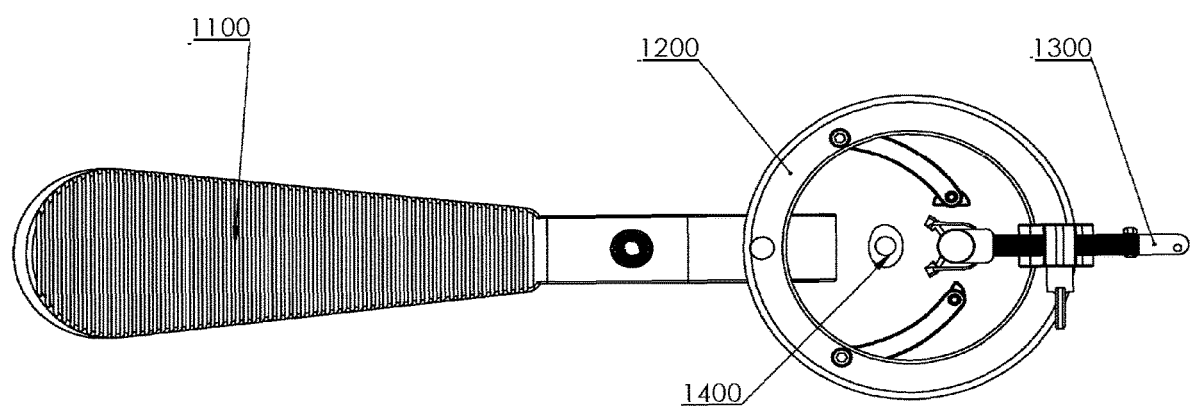
FIG. 10b shows a plan view of the third step in the assembly of an embodiment of a Retractor System.

According to a first embodiment of the present disclosure shown in FIGS. 10a and 10b, a Retractor System 1000 comprises a handheld retractor 1100, with the handheld retractor oriented distally from a ring retractor 1200. Additionally, there is a muscle retractor 1300 capable of optionally coupling to the ring retractor, and a set of stepped dilators 1400 which are sized and shaped to be used within the ring retractor either independently or coupled to the ring retractor with an additional armature.

Figure 2A:
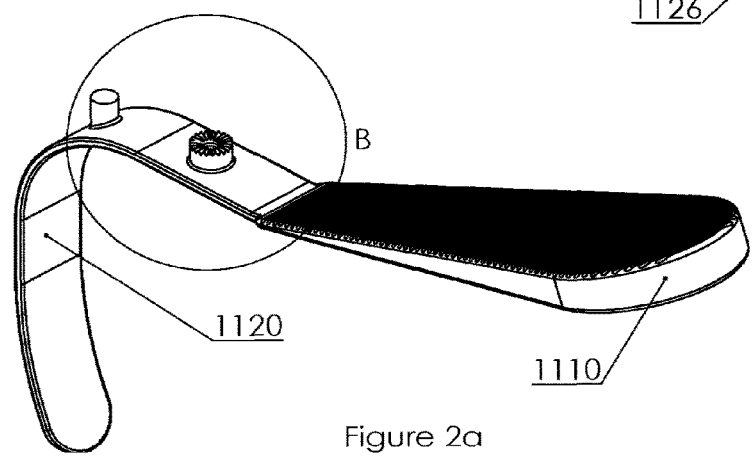
FIG. 2a shows a perspective view of a handheld retractor.
Figure 1:
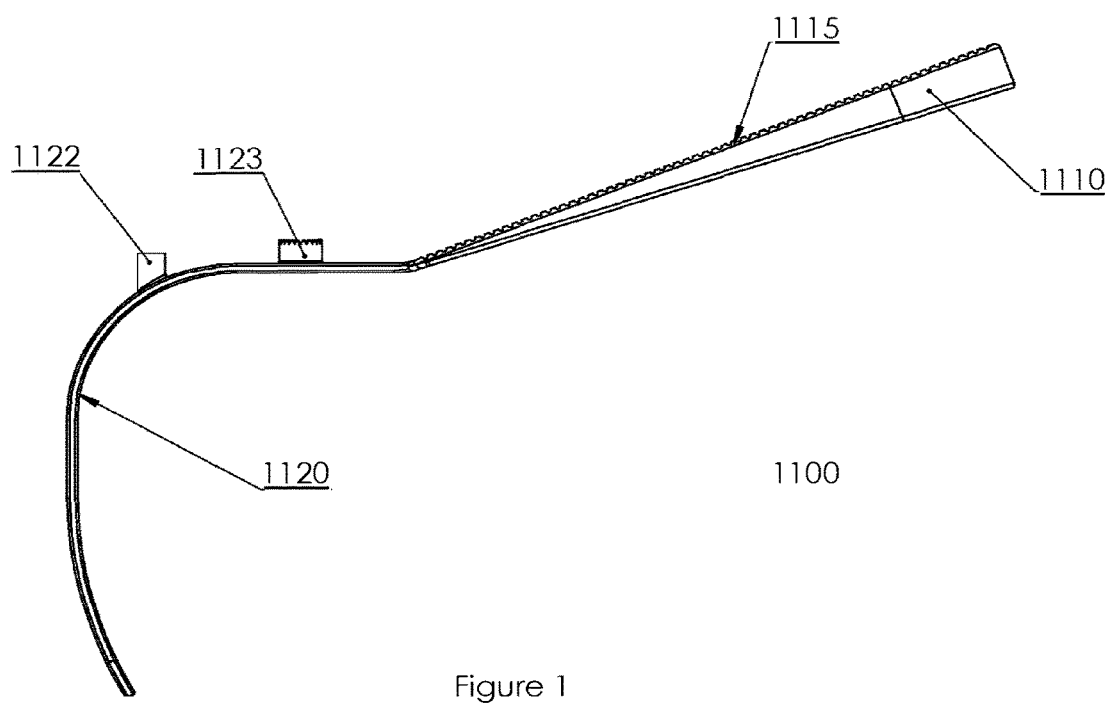
FIG. 1 shows a side view of a handheld retractor.

Referring now to FIGS. 1, 2a, and 2b together, an embodiment of a handheld retractor 1100 is shown wherein the retractor has an arcuate blade 1120 composed of a metal or polymer at a first, distal end thereof and an enlarged hand-grip 1110 at a second, proximal end thereof. Blade 1120 is sized and shaped to manually retract large portions of tissue. According to certain embodiments of the present disclosure, the blade 1120 approximates what is referred to as a Deaver Retractor in the surgical arts. The present invention is distinguishable from existing Deaver Retractors at least in that the mid-section of the retractor 1100 has a plurality of features sized and shaped to couple the device to the remainder of the assembly. These are (1) a smooth post 1122 which is a substantially cylindrical body extending proximally from the blade 1120, (2) a ribbed post 1123 which is a hollow body having a smooth exterior, a thread 1125 about its interior, and a plurality of teeth upon its proximal face sized and shaped to be coupled fixedly to a mirror reflection thereof, and (3) a coupling profile 1126 upon a portion of the retractor 1100 between the blade 1120 and handle 1110 which is sized and shaped to fixably receive a portion of ring retractor 1200 thereupon as will be explained later. Handle 1110 is an enlarged portion of the retractor 1100 having a modified surface texture 1115 upon a portion thereof sized and shaped to improve grip of the device when held by the gloved hand of an operator, including for instance a surgeon.

Referring now to FIGS. 3 and 4 together, stepped dilators 1410 and 1420 are shown which when assembled together define dilator 1400. First dilator 1410 is a small tube having a cannula extending therethrough along a longitudinal axis of the dilator 1410 with the cannula sized and shaped for sliding along a guide wire and a conical tip 1415 near the distal end portion thereof sized and shaped for puncturing tissue. Second dilator 1420 is a larger cross-section tube having an elliptical outer profile and an inner profile sized and shaped to smoothly accommodate the movement of first dilator 1410 therethrough and having a conical tip at the distal end portion thereof with the tip being sized and shaped to puncture and enlarged tissue when pressure is applied thereagainst.

Figure 5:
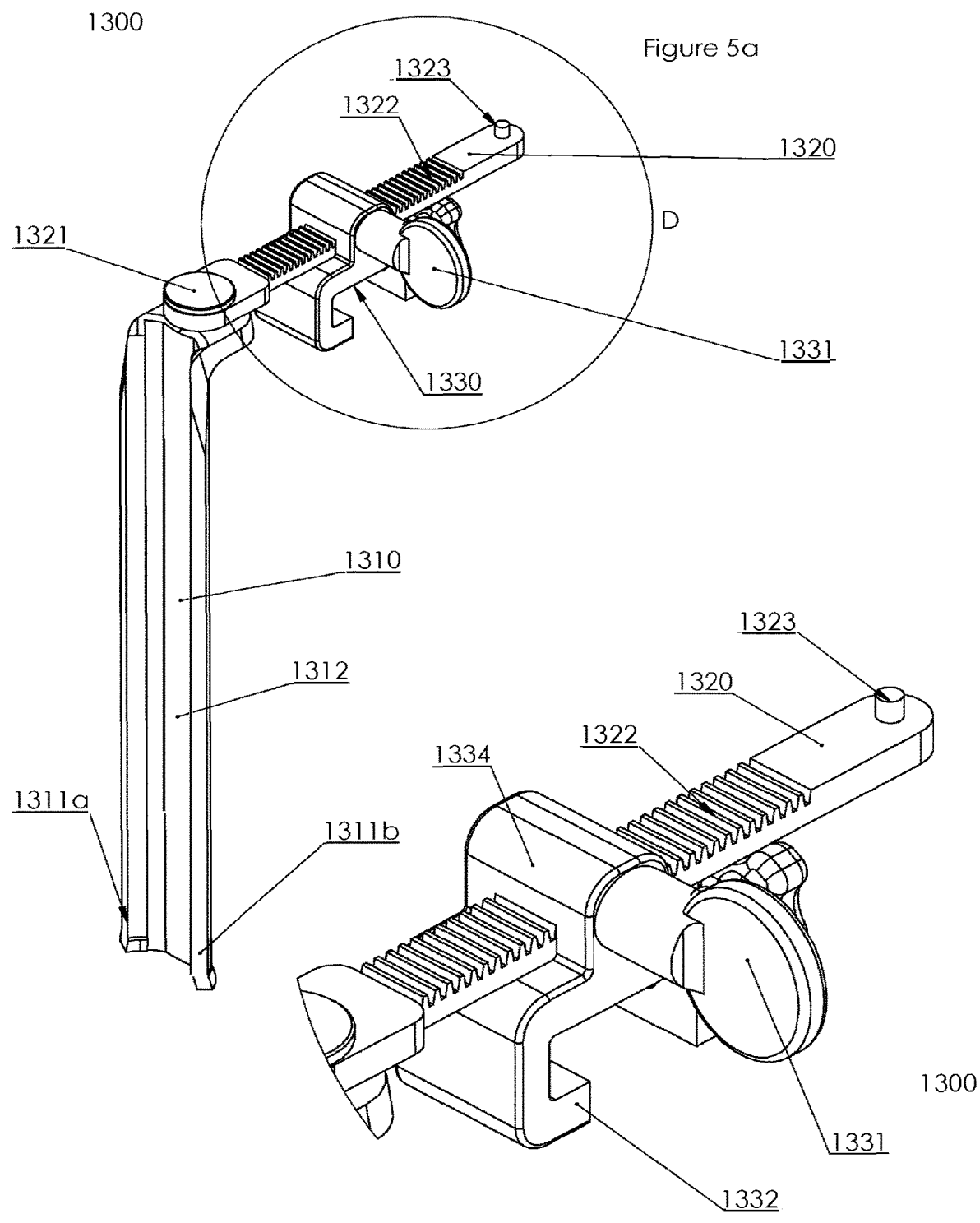
FIG. 5a shows a perspective view of a muscle retractor.
FIG. 5b shows an enlarged perspective view of several coupling features of a muscle retractor.

Referring now to FIGS. 5a and 5b together, a muscle retractor 1300 comprises a blade 1310 pivotably coupled to a linear gear 1320, with the linear gear being movably relative to a clamp 1330.

Blade 1310 is an elongated body comprised of a metal or polymer having a curved cross-section with opposing faces 1311a and 1311b turned inwards towards one another and a connecting surface 1312 disposed therebetween. According to certain embodiments of the present disclosure, there is a ridge at junction of faces 1311 (a and b) and surface 1312 thereby defining a rail upon which additional tools or instrumentation may be slideably coupled. Upon the proximal-end portion blade 1310, there is a bend which provides a location for a pivot 1321.

Linear gear 1320 is an elongated body comprised of metal or polymer having a pivot 1321 coupled to the blade 1310 at a distal end thereof, a pin 1323 extending upward from the proximal end portion thereof and a plurality of teeth defining a gear train 1322 disposed therebetween. Clamp 1330 is positionable upon the length of gear train 1322.

Clamp 1330 has a key 1331 extending therethrough with a finger-grasp at a first end thereof and a spur gear at a second end thereof with the spur gear being engaged upon gear train 1322. The second end of the key is enclosed within a body 1334 and sized and shaped to rotate freely therewithin. Clamp 1332 is sized and shaped to engage upon the body of ring retractor 1200, with rotation of key 1331 defining the position of blade 1310 relative to ring retractor 1200 when the device is assembled.

Figure 6:
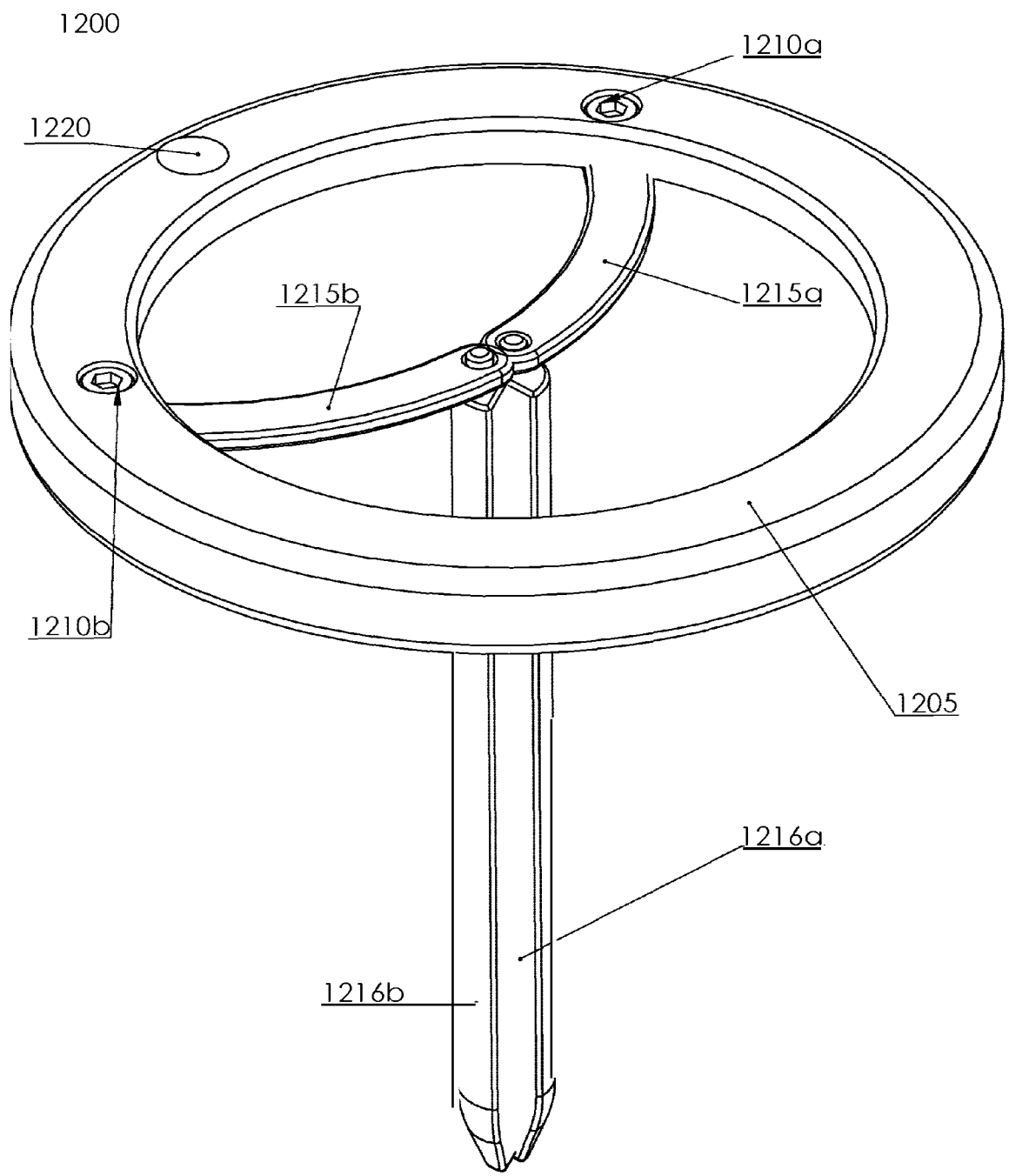
FIG. 6 shows a perspective view of a ring retractor.

Referring now to FIG. 6, a ring retractor 1200 is shown. Ring retractor 1200 comprises a rigid ring 1205 having a coupling aperture 1220 extending therethrough and at least two blade assemblies extending from the distal face thereof, with each blade assembly comprising a threaded pivot bolt 1210 (a and b) coupled to the rigid ring 1205 (a and b) by means of a complementary threaded hole in the ring, an arm 1215 (a and b) pivotably coupled about the pivot bolt 1210 (a and b), with the arm 1215 (a and b) extending from the periphery of rigid ring 1205 to the center thereof and having a retractor blade 1216 (a and b) pivotably coupled to the arm 1215 (a and b) and extending distally therefrom.

Aperture 1220 is sized and shaped to complimentarily receive the post 1122 therewithin.

Figure 7:
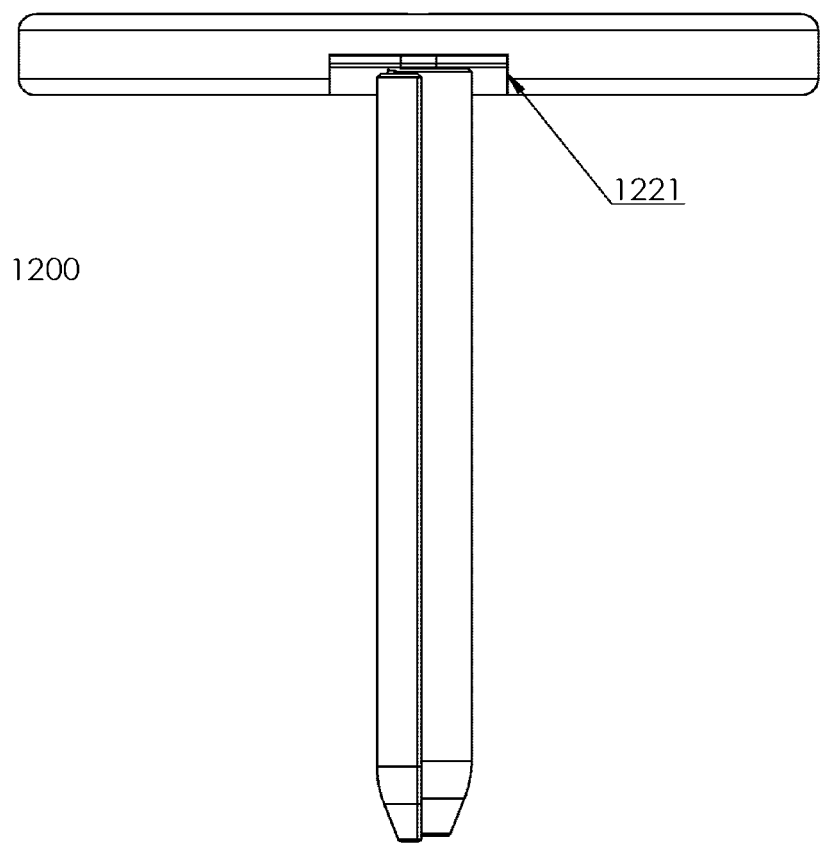
FIG. 7 shows a rear view of a ring retractor.
Figure 8:
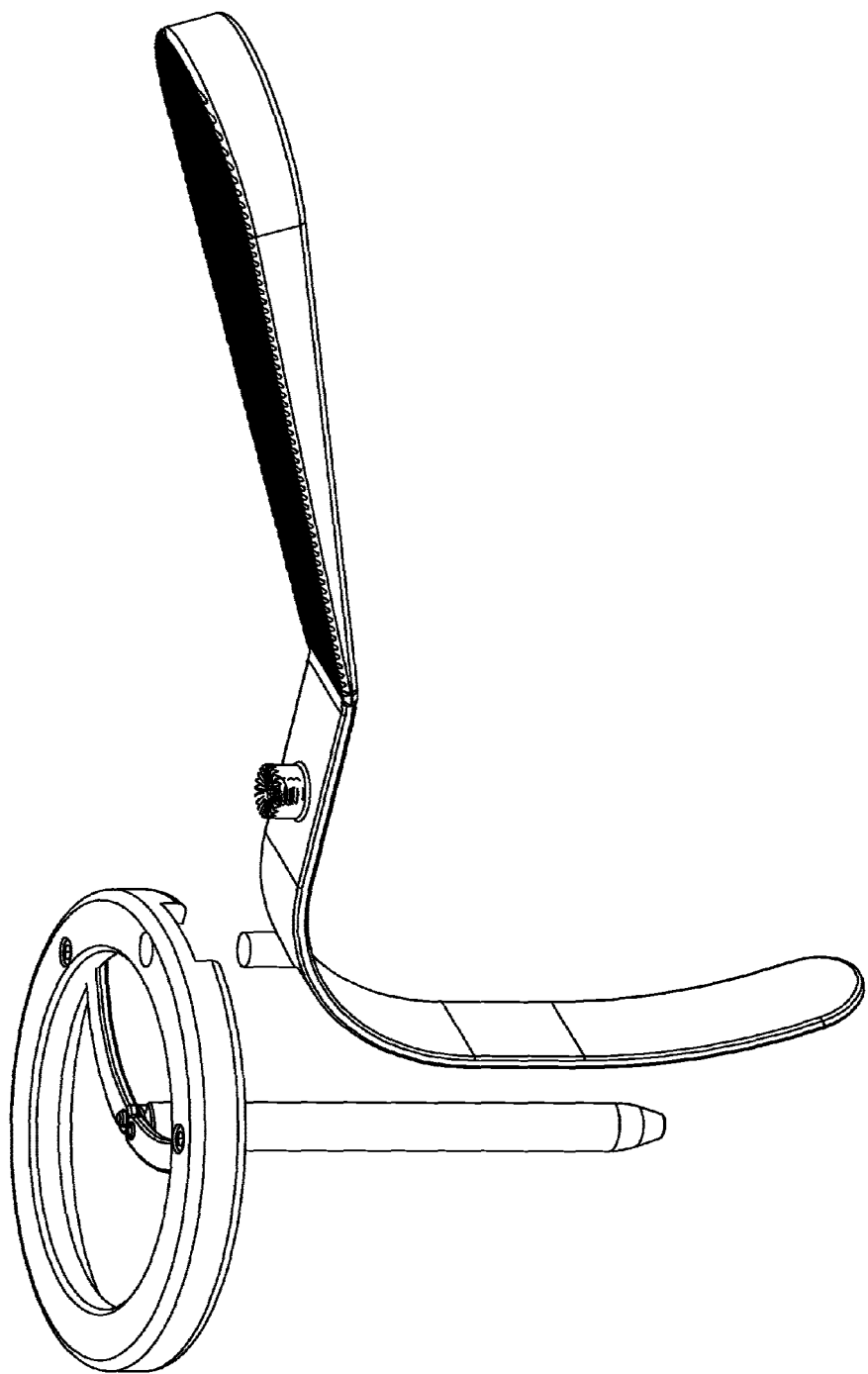
FIG. 8 shows a perspective view of a first step in the assembly of an embodiment of a Retractor System.
Figure 9:
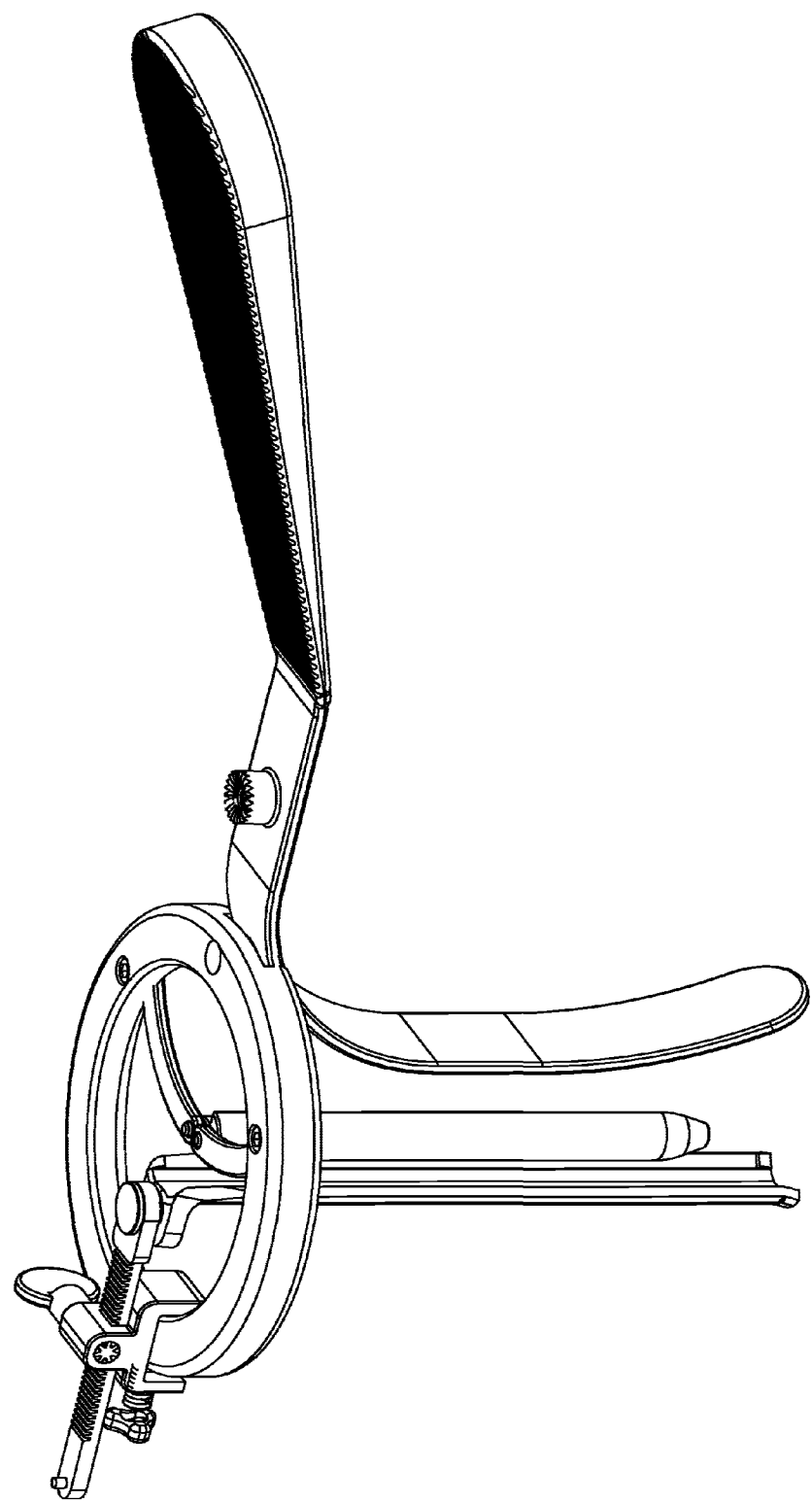
FIG. 9 shows a perspective view of a second step in the assembly of an embodiment of a Retractor System.

Referring now to FIG. 7, a distal cutout 1221 disposed upon the distal face of rigid ring 1205 is shown, where distal cutout 1221 is a portion of material removed from the distal face of the rigid ring 1205 sized and shaped to firmly accommodate coupling profile 1126 therewithin with minimal lateral movement.

A method of assembling and using the present invention will now be described. Initially, a handheld retractor 1100 is provided and grasped about its grip by a surgeon or operator. The blade 1120 is placed into in incision disposed upon a patient's body and the handle of the retractor translated in the general direction of the axis defined by the length of the handle, thereby pulling back tissue layers and partially exposing an operative site. At this stage, the handheld retractor may be mounted to a table arm (not shown) to be held in place about ribbed post 1123 or a table arm clamp engaging about the body of the handheld retractor. Next, the ring retractor 1200 is provided in a "closed" configuration, with the distance between its blades reduced to a minimum. The blades are inserted into the space created by the blade of the handheld retractor and placed atop the handheld retractor such that post 1122 is inserted into aperture 1220 and the opposing vertical sides of distal cutout 1221 abut the sides of coupling profile 1126 such that the ring retractor 1200 is firmly seated upon handheld retractor 1100. According to certain embodiments of the present disclosure, a clamping feature adds rigidity to the coupling of the handheld retractor 1100 to the ring retractor 1200.

Next, the opposing blades 1216 (a and b) of the ring retractor 1200 are manually articulated by an operator into an open configuration wherein a gap is created between them. Once a satisfactory gap has been created, the position of the blades 1216 (a and b) is secured by tightening the bolts 1210 (a and b) against the ring retractor 1200.

Next, the muscle retractor assembly 1300 is inserted into the operative site with the blade 1310 extending into the newly created operative space with the clamp 1330 secured about the body of ring retractor 1200. Finally, the stepped dilators are inserted into the operative space, including for instance the psoas muscle initially about a guidewire placed by the operator, first with dilator 1410 traveling over the guidewire and dilating and first area and finally with the dilator 1420 traveling over dilator 1410 creating the assembly approximated by FIGS. 10a and 10b.

Although the present invention has been described in the section above with reference to specific shaped and structures, one having ordinary skill in the mechanical arts will appreciate that the foregoing is one exemplary implementation of the claims which are appended below.

What is claimed is:

1. A method of preparing an operating site on a patient's body in a surgical environment comprising the steps of:

inserting a blade of a handheld retractor into an incision disposed upon the patient's body, wherein the handheld retractor includes a handle having an axis defined by the length of the handle;
exposing the operating site within the incision by translating the handheld retractor in the general direction of the axis of the handle, away from the incision;
preparing a ring retractor in a closed configuration whereby a first blade assembly and a second blade assembly are rotatably positioned with respect to an armature of the ring retractor such that a distance between a retractor blade of the first assembly and a retractor blade of the second assembly are reduced to a minimum distance;
subsequent to inserting the blade of the handheld retractor into the incision, simultaneously inserting the retractor blades of the first and second blade assemblies into the incision;
seating the ring retractor upon the handheld retractor such that a post extending from the handheld retractor is inserted into an aperture formed in the ring retractor;
articulating the first and second blade assemblies in an open configuration wherein a gap is created between the retractor blades of the first and second blade assemblies;
inserting a blade of a muscle retractor assembly into the incision;
fixing the muscle retractor assembly into position with respect to the ring retractor; and
inserting a plurality of stepped dilators into the operating site.

2. The method of claim 1, wherein the handheld retractor comprises a Deaver Retractor.

3. The method of claim 1, further comprising the step of fixing the handheld retractor into position with respect to the surgical environment.

4. The method of claim 1, further comprising the step of mounting the handheld retractor to a table arm at a second post on the handheld retractor.

5. The method of claim 1, further comprising the step of mounting the handheld retractor to a table arm clamp secured to the handheld retractor.

6. The method of claim 1 further comprising the step of fixing the ring retractor into position with respect to the handheld retractor.

7. The method of claim 1, wherein the step of fixing the muscle retractor assembly into position with respect to the ring retractor comprises securing the muscle retractor assembly to the ring retractor by tightening a clamp of the muscle retractor assembly to the armature of the ring retractor.

8. The method of claim 1, wherein the first and second blade assemblies each comprise an arm pivotally coupled to the armature at a proximal end and extending inwardly from a periphery of the armature to a distal end, a retractor blade pivotally coupled to the arm and extending distally therefrom, and a threaded pivot bolt pivotally coupling the arm to the armature, further comprising the step of fixing the positions of the first and second blade assemblies by tightening the threaded pivot bolt of each of the first and second blade assemblies.

9. The method of claim 1, wherein the blade of the muscle retractor assembly further comprises an elongated body having a curved cross-section with a pair of opposing faces turned inwards towards one another and a connecting surface disposed between the pair of opposing faces.

10. The method of claim 9, wherein the blade of the muscle retractor assembly further comprises a ridge positioned between each of the opposing faces in the pair of opposing faces and the connecting surface, thereby defining a rail.

11. A method of preparing an operating site on a patient's body comprising the steps of:
inserting a blade of a handheld retractor into an incision disposed upon the patient's body, wherein the handheld retractor includes a handle having an axis defined by the length of the handle;
exposing the operating site within the incision by translating the handheld retractor in the general direction of the axis of the handle, away from the incision;
mounting the handheld retractor to a table arm at a first post on the handheld retractor or a table arm clamp secured to the handheld retractor;
preparing a ring retractor in a closed configuration whereby a first blade assembly and a second blade assembly are rotatably positioned with respect to an armature of the ring retractor such that a distance between a retractor blade of the first assembly and a retractor blade of the second assembly are reduced to a minimum distance;
subsequent to inserting the blade of the handheld retractor into the incision, simultaneously inserting the retractor blades of the first and second blade assemblies into the incision;
seating the ring retractor upon the handheld retractor such that a second post extending from the handheld retractor is inserted into an aperture formed in the ring retractor;
manually articulating the first and second blade assemblies in an open configuration wherein a gap is created between the retractor blades of the first and second blade assemblies;
fixing the positions of the first and second blade assemblies by tightening a threaded pivot bolt pivotally coupling each blade assembly to the armature;
inserting a blade of a muscle retractor assembly into the incision;
securing the muscle retractor assembly to the ring retractor by tightening a clamp of the muscle retractor assembly to the armature of the ring retractor; and
inserting a plurality of stepped dilators into the operating site.

12. The method of claim 11, wherein the first and second blade assemblies each comprise an arm pivotally coupled to the armature at a proximal end and extending inwardly from a periphery of the armature to a distal end, a retractor blade pivotally coupled to the arm and extending distally therefrom, and the threaded pivot bolt pivotally coupling the arm to the armature.

13. The method of claim 11, wherein the blade of the muscle retractor assembly further comprises an elongated body having a curved cross-section with a pair of opposing faces turned inwards towards one another and a connecting surface disposed between the pair of opposing faces.

14. The method of claim 13, wherein the blade of the muscle retractor assembly further comprises a ridge positioned between each of the opposing faces in the pair of opposing faces and the connecting surface, thereby defining a rail.

15. A method of preparing an operating site on a patient's body in a surgical environment comprising the steps of:

inserting a blade of a handheld retractor into an incision disposed upon the patient's body, wherein the handheld retractor includes a handle having an axis defined by the length of the handle;

exposing the operating site within the incision by translating the handheld retractor in the general direction of the axis of the handle, away from the incision;

preparing a ring retractor in a closed configuration whereby a first blade assembly and a second blade assembly are rotatably positioned with respect to an armature of the ring retractor such that a distance between a retractor blade of the first assembly and a retractor blade of the second assembly are reduced to a minimum distance;

subsequent to inserting the blade of the handheld retractor into the incision, simultaneously inserting the retractor blades of the first and second blade assemblies into the incision;

articulating the first and second blade assemblies in an open configuration wherein a gap is created between the retractor blades of the first and second blade assemblies;

providing a muscle retractor assembly comprising:
  a clamp having a body;
  a linear gear extending through the body of the clamp, the linear gear comprising:
    a pivot at a distal end of the linear gear;
    an upwardly extending pin at a proximal end of the linear gear; and
    a plurality of teeth defining a gear train disposed between the distal end and the proximal end of the linear gear; and
  a muscle retractor blade pivotally coupled to the pivot of the linear gear;

inserting the muscle retractor blade into the incision; and fixing the muscle retractor assembly to the ring retractor by tightening the clamp of the muscle retractor assembly to the armature of the ring retractor.

16. The method of claim 15, further comprising the step of seating the ring retractor upon the handheld retractor such that a post extending from the handheld retractor is inserted into an aperture formed in the ring retractor.

17. The method of claim 15, wherein the first and second blade assemblies each comprise an arm pivotally coupled to the armature at a proximal end and extending inwardly from a periphery of the armature to a distal end, a retractor blade pivotally coupled to the arm and extending distally therefrom, and a threaded pivot bolt pivotally coupling the arm to the armature, further comprising the step of fixing the positions of the first and second blade assemblies by tightening the threaded pivot bolt of each of the first and second blade assemblies.

18. The method of claim 15, wherein the handheld retractor comprises a Deaver Retractor.

19. The method of claim 15, wherein the muscle retractor blade further comprises an elongated body having a curved cross-section with a pair of opposing faces turned inwards towards one another and a connecting surface disposed between the pair of opposing faces.

* * * * *